United States Patent [19]
Stone et al.

[11] Patent Number: 5,976,462
[45] Date of Patent: Nov. 2, 1999

[54] COMPOSITIONS AND METHOD FOR DISINFECTING FABRIC

[76] Inventors: Ralph P. Stone, 2122 Bay Cove Ct., Arlington, Tex. 76013; Billie M. York, 6532 Castle Pines, Forth Worth, Tex. 76132; Rodney P. Horn, 909 Sugarbush St., Burkburnette, Tex. 76354; Jeffrey S. Kiel, 3541 Mill La., Gainesville, Ga. 30504

[21] Appl. No.: 08/895,844

[22] Filed: Jul. 18, 1997

Related U.S. Application Data

[63] Continuation of application No. 08/552,854, Nov. 3, 1995, abandoned.

[51] Int. Cl.$^6$ ........................................................ A61L 2/18
[52] U.S. Cl. ............................................. 422/28; 424/404
[58] Field of Search ........................ 106/2, 15.05, 18.32, 106/18.35; 252/8.61, 8.62, 32, 36, 37; 424/404, 411; 514/772.3, 643; 428/245, 260, 262, 279, 264, 265, 267, 268, 290; 422/28

[56] References Cited

U.S. PATENT DOCUMENTS

| | | | |
|---|---|---|---|
| 4,801,493 | 1/1989 | Ferziger et al. | 428/268 |
| 5,013,769 | 5/1991 | Murray et al. | 424/78.06 |
| 5,035,943 | 7/1991 | Kinlaw et al. | 428/290 |
| 5,154,920 | 10/1992 | Flesher et al. | 106/15.05 X |
| 5,419,487 | 5/1995 | Nielsen et al. | 239/10 |
| 5,438,076 | 8/1995 | Friedman et al. | 514/772.6 |

OTHER PUBLICATIONS

Block, Seymour S. Disinfection, Sterilzation, and Preservation, 4th ed., pp. 226,227,249 and 250, 1991.

*Primary Examiner*—Elizabeth McKane
*Attorney, Agent, or Firm*—Sally Yeager

[57] ABSTRACT

Compositions for disinfecting fabric and preventing spread of contamination are disclosed. Methods for their use are also contemplated.

4 Claims, No Drawings

COMPOSITIONS AND METHOD FOR DISINFECTING FABRIC

This application is a continuation, of application Ser. No. 08/552,854, filed Nov. 3, 1995, now abandoned.

Infection can be transferred among individuals through contact with physiological fluids of an infected individual. For those individuals who participate in activities in which contact with blood and other physiological fluids are common, the risk of infection is increased. In many activities there is no opportunity to remove the contaminant. For example, medical personnel routinely come in contact with individuals who may have wounds or are otherwise contaminated with physiological materials. The medical personnel are not able to take the time to change their clothes without compromising a patient's well-being. Another example is individuals who are involved in competitive sports. In certain sports, such as football and basketball, participants often have injuries which contaminate their's and other's clothing with blood and other fluids, and it is not feasible for participants to change their uniforms during a game.

The use of anti-infectives to sanitize and disinfect surfaces is well known and there are many products which are marketed in this area. There are also products which are marketed which are used during cleaning procedures which sanitize fabrics. These do not provide a solution to the problem of immediate treatment or protection of clothing during a period where time may be important and other solutions impractical. It would be desirable to have a composition which can be applied to clothing soiled by blood or other body fluids that will disinfect the area on which it is applied as well as provide a physical barrier preventing spread of the infection. The present invention fills this need.

The compositions of the present invention can be sprayed or otherwise applied to clothing to provide for anti-infective action against bacteria and viruses and at the same time form a physical barrier to prevent the spread of contamination.

The compositions comprise known viricides/biocides ("antimicrobial agent"), such as: aldehydes (glutaraldehyde, acetaldehyde, crotonaldehyde); alcohols, which can also function as a solvent, (ethanol, methanol, isopropanol); quaternary ammonium compounds (benzalkonium chloride, benzethonium chloride, tallow triethanol ammonium chloride); and phenols (phenol, resorcinol, and cresol). The compositions also include a polymeric barrier producing agent. The barrier producing agent is one or more polymeric materials which when dried forms a surface which is resistant to water and serves as a barrier preventing the spread of microorganisms. Examples of such polymeric materials are polyethylene glycol 8000 (carbowax 8000), derivatives of polyvinyl pyrrolidinone, alkyl quaternary polymers, derivatives of hydroxyethyl methacrylate and polylactic acid, and polyoxyethylene polyoxypropylene copolymers, such as, Pluronic and Tetronic. The key consideration for the selection of the polymer is that it form a water resistant barrier under the conditions in which the fabric is used, e.g., during athletic activities, but can then be removed under normal laundry conditions.

The antimicrobial agents and barrier producing agents are marketed by numerous vendors and are readily available. These materials are combined in a suitable solvent system for application to fabric. The solvent system must be such that it will dissolve the active ingredients, but evaporate relatively quickly leaving the polymer to form the barrier discussed above.

The following examples are not meant to be limiting.

EXAMPLE 1

The following solution was prepared:

| | |
|---|---|
| Benzalkonium Chloride | 0.5% |
| Ethanol | 60.00% |
| Polyethylene glycol 8000 | 20.00% |
| Water | 19.95% |

The solution was placed in a spray bottle and applied to a fabric surface. The solution was allowed to dry. A water resistant barrier formed.

EXAMPLE 2

The following solution was prepared:

| | |
|---|---|
| Benzalkonium chloride | 0.10% |
| Ethanol | 60.00% |
| Acetone | 10.00% |
| Pluronic | 20.00% |
| Water | 9.90% |

The compositions of the present invention are applied directly to contaminated fabric and the composition allowed to dry.

We claim:

1. A composition for disinfecting fabric contaminated with physiological fluids comprising an anti-infective amount of at least one antimicrobial agent selected from the group consisting of benzalkonium chloride, benzethonium chloride, tallow triethanol ammonium chloride, phenol, resorcinol, cresol, ethanol, methanol, isopropanol, glutaraldehyde, acetaldehyde, and crotonaldehyde and a polymeric material which when dried forms a barrier resistant to water selected from the group consisting of polyethylene glycol, polymers of polyvinyl pyrrolidinone, alkyl quaternary polymers, polymers of hydroxyethyl methacrylate, polylactic acid, polyoxyethylene, and polyoxyethylene copolymers, said composition being removable from the fabric under normal laundry conditions.

2. The composition of claim 1 wherein there are two antimicrobial agents, benzalkonium chloride and ethanol and the polymeric material is polyethylene glycol.

3. A method for disinfecting fabric after it becomes contaminated with physiological fluids which comprises applying a composition comprising an anti-infective amount of at least one antimicrobial agent selected from the group consisting of benzalkonium chloride, benzethonium chloride, tallow triethanol ammonium chloride, phenol, resorcinol, cresol, ethanol, methanol, isopropanol, glutaraldehyde, acetaldehyde, and crotonaldehyde and a polymeric material which when dried forms a barrier resistant to water selected from the group consisting of polyethylene glycol, polymers of polyvinyl pyrrolidinone, alkyl quaternary polymers, polymers of hydroxyethyl methacrylate, polylactic acid, polyoxyethylene, and polyoxyethylene copolymers, said composition being removable from the fabric under normal laundry conditions.

4. The method of claim 3 wherein there are two antimicrobial agents, benzalkonium chloride and ethanol and the polymeric material is polyethylene glycol.

* * * * *